US012702823B2

(12) United States Patent
Tellenbach et al.

(10) Patent No.: US 12,702,823 B2
(45) Date of Patent: Aug. 11, 2026

(54) DEVICES FOR NEUROMUSCULAR ELECTRICAL STIMULATION

(71) Applicant: NMES Group AB, Svenljunga (SE)

(72) Inventors: Vincent Tellenbach, Sion Valais (CH); Heiko Van Vliet, Chêne (CH); Jeffrey Fu Hsu, Taiwan City (TW); Mathias Jepson, Svenljunga (SE); Richard Charles Statham, Boras (SE); Vedran Stankovic, London (GB)

(73) Assignee: NMES Group AB, Svenljunga (SE)

( * ) Notice: Subject to any disclaimer, the term of this patent is extended or adjusted under 35 U.S.C. 154(b) by 130 days.

(21) Appl. No.: 18/274,440

(22) PCT Filed: Jan. 27, 2022

(86) PCT No.: PCT/EP2022/051963

§ 371 (c)(1),
(2) Date: Jul. 26, 2023

(87) PCT Pub. No.: WO2022/162099

PCT Pub. Date: Aug. 4, 2022

(65) Prior Publication Data

US 2024/0165400 A1 May 23, 2024

Related U.S. Application Data

(60) Provisional application No. 63/199,810, filed on Jan. 27, 2021.

(51) Int. Cl.

| | |
|---|---|
| ***A61N 1/04*** | (2006.01) |
| ***A61N 1/36*** | (2006.01) |
| ***G16H 40/63*** | (2018.01) |

(52) U.S. Cl.
CPC ....... *A61N 1/0484* (2013.01); *A61N 1/36003* (2013.01); *A61N 1/3603* (2017.08); *G16H 40/63* (2018.01)

(58) Field of Classification Search
CPC ............................ A61N 1/0484; A61N 1/3603
(Continued)

(56) References Cited

U.S. PATENT DOCUMENTS

| | | | |
|---|---|---|---|
| 2014/0276298 A1 | 9/2014 | Coleman et al. | |
| 2017/0181703 A1 | 6/2017 | Kaib et al. | |

FOREIGN PATENT DOCUMENTS

| | | | |
|---|---|---|---|
| DE | 102015113420 A1 * | 2/2017 | ........... A61N 1/3603 |
| EP | 3148633 A1 | 4/2017 | |

OTHER PUBLICATIONS

PCT/EP2022/051963, May 19, 2022, International Search Report.
(Continued)

*Primary Examiner* — Nadia A Mahmood
(74) *Attorney, Agent, or Firm* — Wolf, Greenfield & Sacks, P.C.

(57) ABSTRACT

A system for providing wireless electrical stimulation to muscles and nerves for the treatment of medical and non-medical conditions. The electrical stimulation is delivered to the stimulated object (individual) by small neuromuscular electrical stimulation devices attached to wearable supports featuring electrically conductive material rendered on the inside and acting as electrodes. The control of the electrical stimulation devices is provided by a dedicated application running on a mobile device by means of a Bluetooth Low Energy interface.

18 Claims, 14 Drawing Sheets

(58) Field of Classification Search
USPC .............................................................. 607/48
See application file for complete search history.

(56) References Cited

OTHER PUBLICATIONS

International Search Report and Written Opinion dated May 19, 2022, in connection with International Application No. PCT/EP2022/051963.

Communication in cases for which no other form is applicable dated Jun. 3, 2022, in connection with International Application No. PCT/EP2022/051963.

* cited by examiner

Front Right Back Left 301 301 303 306 306 303

302 302 304 305 307 308 308 307 305 304

DEVICES FOR NEUROMUSCULAR ELECTRICAL STIMULATION

CROSS REFERENCE TO RELATED APPLICATIONS

This Application is a national stage filing under 35 U.S.C. § 371 of International Patent Application Serial No. PCT/EP2022/051963, filed on Jan. 27, 2022, entitled DEVICES FOR NEUROMUSCULAR ELECTRICAL STIMULATION, which claims the benefit of U.S. Provisional Application No. 63/199,810, filed on Jan. 27, 2021. The contents of these applications are incorporated herein by reference in their entirety.

FIELD OF THE INVENTION

The present invention relates, in general, to the use of electrical stimulation of muscles and nerves for the purpose of alleviating a broad range of medical conditions as well as for specific non-medical objectives.

BACKGROUND

The number of medical applications that use electrical stimulation is large and covers virtually every living body component. These applications include prevention of muscle atrophy, promotion of wound healing, prevention of venous thrombosis, alleviation of both chronic/acute pain and prevention of incontinence to name but a few. Electrical stimulation may also be used for such non-medical objectives as muscle training, muscle toning, improving muscle endurance, and muscle relaxation.

Electrical stimulation of muscles and nerves is well established in medicine and physical therapy with a history dating back to mid-1850; such stimulation is currently achieved by applying electrodes to: 1) the skin at the point(s) of desired electrical stimulation; 2) through insertion of electrical probes into body cavities, and; 3) through surgical insertion of electrodes.

Electrical stimulation of muscles and nerves consists in the delivery of short duration electrical impulses. These impulses can be controlled (or regulated) in voltage or electrical current. Both technologies have their own advantages and disadvantages. Electrical current regulation is better suited for precise electrical stimulation requiring small electrodes while voltage regulation is better suited for larger electrodes or electrodes that slightly move on the skin.

Neuromuscular Electrical Stimulation Principle

Muscle contractions are produced and controlled by the brain by means of electrical signals transmitted through the nervous system. When an electrical signal from the brain reaches the muscle, the latter is activated into groups of "motor units", each made up of a single neuron and of a group of associated muscle cells connected to it. This initiates a chemical reaction which causes the cells in this motor unit to contract. The complete contraction of the muscle usually involves a number of motor units simultaneously, and its strength is directly proportional to the number of activated motor units. The gradual enrolment process of the motor units which consents to a perfectly controlled and smooth muscle contraction is called spatial summation.

Electrical muscle stimulation (EMS), also known as neuromuscular electrical stimulation (NMES) or electromyostimulation, is the elicitation of muscle contraction using electric impulses. The impulses are generated by a device and are delivered through electrodes on the skin near to the muscles being stimulated. The electrodes are generally pads that adhere to the skin. The impulses mimic the action potential that comes from the central nervous system, causing the muscles to contract.

When a sufficiently intense single electrical impulse reaches the motor muscle or nerve, it causes one short single contraction of the muscle (spasm). If this single spasm is repeated and the frequency of reiteration exceeds ten spasms p.s., each following spasm is enhanced by one degree of muscle shortening caused by the preceding spasm. Such an effect is called temporal summation. The lowest stimulation frequency, where the successive contractions merge, is called tetanization frequency.

Devices for providing NMES are often controlled by a wired connection to a control unit into which stimulation programs can be pre-programmed and/or user selected. Such control units may have ports for wires which connect to stimulation pads, and thus suffer from certain drawbacks in some applications.

SUMMARY

The invention is defined by the appended independent claims. Embodiments of the invention are defined in the dependent claims.

In a first aspect, there is provided a controller device for controlling provision of electrical stimulation to a user, the controller device being configured to connect electrically to a wearable support, the device comprising: a support connector configured to receive a complimentary device connector of the wearable support, wherein the support connector is configured to permit releasable mounting of the controller device on the wearable support; and a processor configured to receive data from an identifier on the wearable support.

In this way, the invention provides a controller device suitable for reversible connection, e.g. a clip in mounting, to a wearable support configured to provide electrical stimulation to a user. This is advantageous for a number of reasons.

Firstly, by maintaining a secure connection directly to the wearable support, wired connections which are so limiting for conventional NMES devices and electrode pads can be eliminated. Secondly, one controller device can easily and efficiently be used by a number of different wearable supports. In other words, the controller device is flexible in its applications and can be easily mounted onto different parts of the user's body. This could be helpful during in a medical setting, for example, because treatments can be applied in quick succession to different areas of the body, providing flexibility for medical professionals or users themselves in selecting treatments. In a recreational setting, for example a gym, the controller device can easily be moved from one body part to another in tandem with the progression of the exercises being performed by the user. For example, if a user were to alternate sets of training biceps and triceps, and had access to only two controller devices (one for each arm), the controller devices can be switched between muscle groups very easily and quickly.

The support connector may, advantageously, be configured to achieve a mechanical and/or magnetic snap fit to the device connector on the wearable support. The support connector may be a male connector-type or a female connector-type, and the device connector on the wearable support may therefore be a respective female or male connector-type, in order that the connectors compliment one another to provide releasable mounting.

Electrical connection between the controller device and the wearable support may be achieved in any manner apparent to the skilled person, including, for example, electrical contacts on the controller and support, short wires (still advantageously space efficient due to proximity of controller and support via the mounting), and so on.

Providing a processor configured to receive data from an identifier on the wearable support is advantageous because feedback can be given to the controller device. Feedback could be as simple as verification that the controller device is securely connected via an identifier in the support connector. Feedback could also include data providing information about the identifier on the wearable support, such as its location.

A controller device may be referred to herein as an NMES device.

The controller device may further comprise one or more user controls for controlling provision of electrical stimulation to the user, optionally wherein the one or more user controls comprise one or more of: an on button; an off button; an on/off button; an intensity increase button; and an intensity decrease button.

In this way, the user can control electrical stimulation directly from the controller device, and/or adjust stimulation being provided from an external source (for example turning the intensity up or down). On and off may be understood in this context to be initiation or cessation of an electrical stimulation.

The controller device may further comprise a power source, optionally wherein the power source comprises a rechargeable battery.

In this way, the controller device need not be connected to mains power in order to deliver the electrical stimulation, benefitting its portability and ease of use. These are particularly relevant for devices which can advantageously be mounted directly onto a wearable support.

The controller device may further comprise a visual indicator, optionally wherein the visual indicator comprises a strip of light emitting diodes.

The visual indicator may indicate remaining power level, for example battery charge, progress through a stimulation program, may indicate complete or incomplete attachment of the controller device to the wearable support, or any other parameter useful to the user.

The processor may be further configured to initiate an electrical stimulation program.

The controller device may further comprise a pulse generator configured to provide electrical current to the user via the wearable support. As used herein, an electrical stimulation program may be defined as provision of pulsed electrical current. The pulsed electrical current is supplied from the pulse generator, via the wearable support (for example through conductive media in the wearable support), into the user's skin.

The support connector may be configured such that, when the controller device is mounted on the wearable support, an electrical connection is established between the controller device and the wearable support via the support connector and the device connector.

In this way, the number of connections between controller device and wearable support can be minimised and made more efficient, by achieving both mechanical and electrical connection through the same connector.

The controller device of any preceding claim, wherein the processor is configured to receive data from the wearable support by reading an identifier on the wearable support via a near field communication protocol, optionally wherein the near field communication protocol is radio frequency identification.

Near field communication (NFC) is particularly efficient because the mounting of controller to support ensures that there is close proximity between the two. The lower power requirements of NFC versus other communication types are therefore gained, while the limitations on distance of communication are not significant for this application. RFID has been found to be particularly effective, not least because it removes the need for bulky hardware in the wearable support which, by virtue of being wearable, is better kept light.

In a second aspect, there is provided a wearable support for facilitating provision of electrical stimulation to a user, the wearable support being configured to connect electrically to a controller device, the wearable support comprising: a device connector configured to receive a complimentary support connector of the controller device, wherein the device connector is configured to permit releasable mounting of the controller device on the wearable support; and an identifier, configured to provide data to a processor on the controller device.

Advantages provided by the wearable support are analogous to the advantages provided by the controller device of the first aspect. In particular, the device connector allows reversible mounting attachment of the controller device, facilitating the flexible application of the controller device. Similarly, the identifier allows useful information to be provided to the controller device.

The identifier may be any hardware component capable of providing information to the processor. The identifier may, for example, comprise a memory storing the relevant data and a transmitter, and be configured to transmit the data continuously or intermittently from the transmitter, to be picked up by the processor of the controller device. In such examples the identifier may comprise a power source. Alternatively, the identifier may comprise a passive antenna, configured to have a current induced therein by a reader on the controller device, thereby providing sufficient power to the antenna to transmit a response to the controller device. The need for an identifier power source would therefore be circumvented. Any hardware component capable of providing information to the controller device is suitable for use as an identifier. Similarly, any component suitable to read such an identifier is suitable to be used, in connection with the processor, by the controller device to read the data on the identifier. The controller device may therefore comprise a receiver, to receive a powered transmission from the identifier in certain embodiments. In other embodiments, the controller device may comprise a transmitter, for example a radio frequency transmitter, suitable to power a passive antenna on the identifier, and a receiver suitable to receive any induced data transmission from the identifier. Alternative component architecture will be apparent to the person skilled in the art.

Data may be encoded onto the identifier in a step preceding the methods of data transmission and/or retrieval from the identifier by the processor of the controller device. Data may be encoded onto the identifier in any suitable manner as will be apparent to the skilled person. Specific encoders (for example an RFID printer encoder) may be used for specific identifiers. Alternatively, for identifiers having a local memory, the local memory may simply be written in any suitable manner, for example by a wireless or wired write operation. The data encoded onto the identifier may be the data then transmitted to the controller device, including, but not limited to, a location of the identifier on the wearable support and/or a type of wearable support.

The wearable support may further comprise a conductive medium configured to contact the user and apply the electrical stimulation.

The wearable support may comprise a garment or a wearable accessory, optionally wherein the garment or wearable accessory is: a shirt; pants; a glove; a sock; a strap; a wrap; or a sleeve.

The conductive medium may be embedded within the garment or wearable accessory.

These examples of wearable support are particularly effective for facilitating provision of electrical stimulation to a user. Not only may wearable supports such as these be more comfortable than other methods of applying electrode pads (which may involve irritant adhesives, for example), but they also remove the need for re-application of pads for every stimulation session, and retain the conductive media in specific locations on the body. This is effective for a number of reasons. For example, a medical professional or personal trainer providing virtual care or training, respectively, can be sure that stimulation is being applied to the correct part of the body, because the pads are fixed with respect to the support. Pants as used herein are intended to refer to over-garments worn on the lower body, i.e. garments which may also be referred to as trousers.

The conductive medium may comprise an electrode pad, optionally wherein the electrode pad comprises: a carbon-based electrode; a graphene-based electrode; and/or conductive ink.

As will be discussed in greater detail herein, flexibility of the wearable support while maintaining good electrical contact can be achieved with certain materials, for example carbon, graphene, and conductive ink.

The conductive medium and the identifier may be located in proximity to one another on the wearable support. In this way, an identifier may be associated with a specific conductive medium. This is advantageous because it provides more options as to the data that can be provided by the identifier, as will be discussed in further detail herein.

The device connector may be configured such that, when the controller device is mounted on the wearable support, an electrical connection is established between the controller device and the wearable support via the support connector and the device connector. This is advantageous for the reasons discussed in relation to the support connector.

The identifier may be configured to provide data to the controller device by being configured to be read via a near field communication protocol, optionally wherein the identifier is a radio frequency identification tag. This is advantageous for the reasons discussed in relation to RFID above.

The data provided by the identifier to the controller device may comprise a location of the identifier on the wearable support and/or the type of wearable support. The location may be an identifier of the type of wearable support (meaning whether the support is a sock or a strap, for example), if, for example, the wearable support comprises only one identifier, so identification of the type of support is sufficient to identify the location of the conductive medium. A glove designed to stimulate only one part of the hand and having only one conductive medium and identifier, for example, would provide the location of its conductive medium with only its type. A shirt having multiple identifiers, on the other hand, may provide a location of the identifier on the shirt, for example identifying the right shoulder.

In this way, the controller device can be aware of the location on the wearable support at which it is mounted. The controller device itself may comprise computational instructions which respond to this information, for example limiting the electrical stimulation programs and/or intensities available, or may pass this information to a further device for processing.

The wearable support may further comprise one or more further identifiers, each configured to provide data to a processor on a controller device, and one or more further conductive media, each configured to contact the user and apply electrical stimulation, wherein each further conductive medium is located in proximity to a respective one of the further identifiers on the wearable support.

In this way, a single wearable support can provide a number of sites for controller device connection, and the location of each may be retrievable by the controller devices. At each site, electrical stimulation can be provided via the conductive medium. It will be appreciated that one or more device connectors may be provided at each site, i.e., associated with and proximal to a respective conductive medium and respective identifier. More than one device connector may be provided at each site in order to ensure proper connection and/or to fix orientation of the controller device.

In a third aspect, there is provided a system, comprising: a controller device for controlling provision of electrical stimulation to a user according to the first aspect; and a wearable support for facilitating provision of electrical stimulation to a user according to the second aspect.

There may be multiple controller devices connected to a single wearable support. There may also be multiple conductive media associated with a single identifier, and therefore with a single controller device. The number of conductive media per identifier may depend on the location of the conductive media on the support, for example due to the specifics of the muscle group to be stimulated.

The system may further comprise: a mobile device, in communication with the controller device, the mobile device being configured to receive data from the controller device and to transmit data to the controller device. In this way, a mobile device can control the electrical stimulations provided to the user. This is advantageous because it allows the controller devices to be more efficient and perhaps smaller, since they need only to mount to the support, provide electrical current, read the RFID tag, and communicate with the mobile device. They do not then need, for example, to comprise a display or user input features.

The mobile device and controller device may be configured to communicate via Bluetooth Low Energy. This has been found to be a particularly effective communications protocol for communication between mobile devices and controlling devices, because it is secure and low energy.

In a fourth aspect, there is provided a computer-implemented method, comprising: receiving data identifying a selected type of wearable support; prompting a user to connect a controller device to the selected wearable support; and initiating, in response to user input, an electrical stimulation program by instructing the controller device to deliver electrical current through the selected wearable support.

In this way, the NMES system can be set up and controlled from a mobile device. The user may select the type of wearable support they are wearing, for example a shirt, be prompted to position a controller device in a specific position, and then begin a safe and effective electrical stimulation.

The computer-implemented method may further comprise one or more of: displaying a list of connected controller devices; receiving, from one or more connected controller devices, a level of remaining battery power, and displaying the level of remaining battery power of each controller device; and ceasing, in response to user input, an electrical stimulation program by instructing all connected controller devices to cease delivering electrical current.

In a fifth aspect, there is provided a computer program comprising instructions which, when the program is executed by a computer, cause the computer to carry out the steps of the method of the fourth aspect. The computer program may, for example, be a mobile application.

In a sixth aspect, there is provided a computer-readable data carrier having stored thereon the computer program of the fifth aspect.

Methods according to the invention, as described herein, may be computer-implemented methods and may be used, where appropriate, for the delivery of electrical stimulation impulses for non-medical, or non-clinical, purposes, for example muscle conditioning.

The present invention may be used to treat or improve any muscular or neural condition that is alleviated through use of electrical stimulation.

The foregoing and other objects and advantages will appear from the descriptions that follow. In the description reference is made to the accompanying drawings, which forms a part hereof, and in which is shown by way of illustration specific principles of the control method in which the invention may be practiced. These principles will be described in sufficient detail to enable those skilled in the art to practice the invention, and it is to be understood that other principles may be utilized and that structural changes may be made without departing from the scope of the invention, for example, modifications in algorithms.

It is an object of the present invention to provide a system for the safe and effective electrical stimulation of muscles and nerves that uses wireless neuromuscular electrical stimulation devices.

It is an object of the present invention to provide a system where one or multiple wireless neuromuscular electrical stimulation devices are attached to one or multiple wearable supports which may be, among other things, a body suit, a shirt, pants, gloves, socks, a strap or a sleeve. It is an object of the present invention to provide a system whereby the electrical stimulation is delivered to the stimulated object (individual) by means of electrically conductive materials rendered into garments or accessories.

It is an object of the present invention to provide a system allowing the wireless control of multiple neuromuscular electrical stimulation devices by one application running on a mobile device using the Bluetooth Low Energy (BLE) area network technology.

It is an object of the present invention to provide a system for the delivery of neuromuscular electrical stimulation using preferably voltage regulated technology to provide a constant density of electrical current regardless of the size of the medium through which the electrical stimulation is transferred to the stimulated object (individual).

It is an object of the present invention to provide a system allowing the temporal synchronization of multiple neuromuscular electrical stimulation devices connected by means of the Bluetooth Low Energy (BLE) area network technology to the same application running on a mobile device such as a smartphone or a tablet. It is the object of the present invention to provide a system preserving the stretchability and flexibility of the wearable supports by using a specific design applied to the electrically conductive materials rendered into the wearable supports.

It is an object of the present invention to provide a system allowing the reliable and safe attachment of the neuromuscular electrical stimulation devices to the wearable support by means of connectors which can be of the magnetic or mechanical type.

It is an object of the present invention to provide a system for the delivery of neuromuscular electrical stimulation which can be integrated into other existing systems for the treatment or improvement of muscular or medical condition.

It is an object of the present invention to provide a system for the delivery of neuromuscular electrical stimulation which can be integrated into in a virtual environment for the treatment of muscular or medical condition as well as for gaming or entertainment purposes.

It is an object of the present invention to provide neuromuscular electrical stimulation delivery that overcomes shortcomings in prior art devices.

It is an object of the present invention to provide a system that delivers electrical impulses that trigger strong, effective muscle contractions or nerve responses in a stimulated object (individual).

Another object of the present invention is to provide a neuromuscular electrical stimulation system that may be safely operated by untrained and trained users.

A further object of the present invention is to provide a neuromuscular electrical stimulation that is simple and safe to use A still further object of the present invention is to provide neuromuscular electrical stimulation that is cost and size effective.

DETAILED DESCRIPTION

Figure 1:
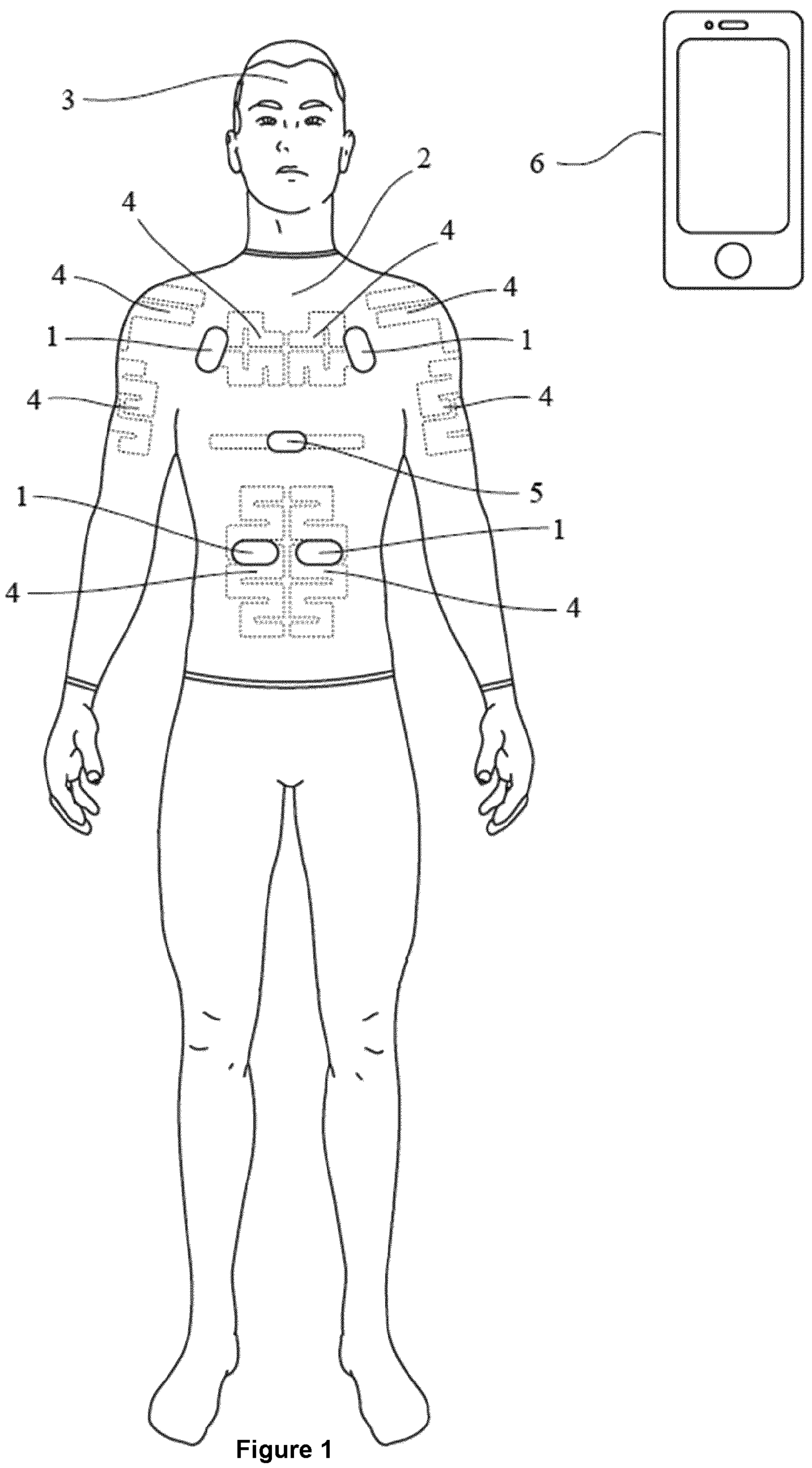
FIG. 1 shows a wearable support, a shirt, in accordance with an embodiment of the invention.

The present invention consists of a system where neuromuscular electrical stimulators (NMES) devices controlled by a mobile application are attached to a garment, strap, wrap or sleeve in order to deliver electrical stimulation to an individual. The system can be divided into three main components:

1. NMES devices
2. Wearable supports with conductive material such as shirt, pants, strap, wrap or sleeve
3. Mobile Application FIG. 1 shows a first embodiment of the invention. Neuromuscular electrical stimulation devices (1) are attached to a shirt (2) worn by an individual (3). The electrical impulses generated by the stimulation devices (1) are safely and effectively transferred to the individual's (3) nerves and muscles by means of electrically conductive electrodes (4) rendered inside the shirt. The design of the electrodes (4) preserves the stretchability of the shirt. The heart rate of the individual (3) can be monitored by an additional heart rate sensor (5) attached to the shirt. The Neuromuscular electrical stimulation devices (1) are connected through the Bluetooth Low Energy and controlled by a dedicated application running on a mobile device (6).

Figure 2:
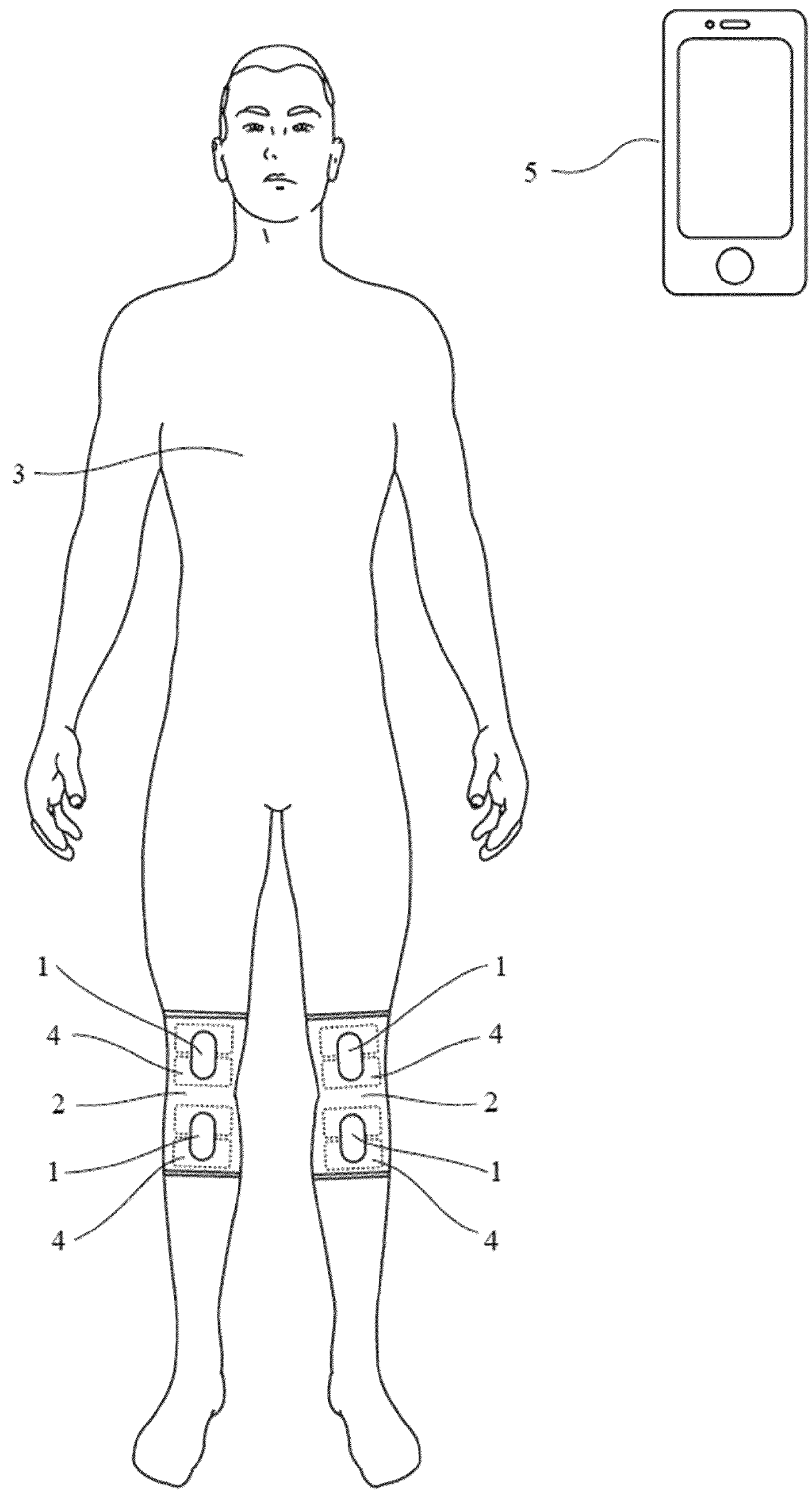
FIG. 2 shows a pair of wearable supports, knee sleeves, in accordance with an embodiment of the invention.

FIG. 2 shows a second embodiment of the invention. Neuromuscular electrical stimulation devices (1) are attached to knee sleeves (2) worn by an individual (3). The electrical impulses generated by the stimulation devices (1) are transferred to the individual (3) knee nerves and muscles by means of electrically conductive electrodes (4) rendered inside the knee sleeve. The Neuromuscular electrical stimulation devices (1) are connected through the Bluetooth Low Energy and controlled by a dedicated application running on a mobile device (5).

NMES Device

Figures 3, 4:
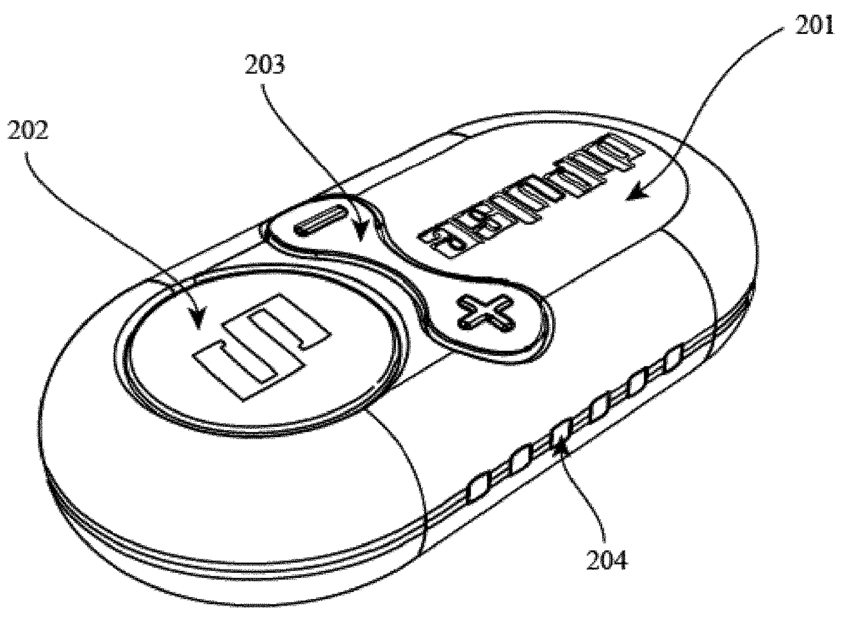
FIG. 3 shows a controller device in accordance with an embodiment of the invention.
FIG. 4 shows four views of a wearable support, a shirt, in accordance with an embodiment of the invention.

FIG. 3 shows an NMES device according to embodiments of the invention, showing device on-board controls (also referred to herein as one or more user controls). The NMES device is a small, portable electronic unit with the principal purpose of delivering safe and efficient electrical stimulation to an individual. It attaches to a wearable support by means of magnetic or mechanical snaps which are electrically connected to conductive material rendered on the inner layer of the wearable support.

The electrical stimulation signal delivered by the NMES device consists of short rectangular shaped impulses regulated either in voltage or electrical current. The impulse's parameters, such as amplitude, impulse duration, and frequency, determine the type of treatment applied to the muscles and nerves of the stimulated individual.

The NMES device connects to a mobile application by means of a Bluetooth Lew Energy (BLE) link. Multiple NMES devices can be connected at the same time during a session. The user controls the NMES devices from the mobile application. The NMES device can also offer on-board controls allowing the user to switch the NMES device on and off, select and start a stimulation program, set the stimulation intensity, and visualize the intensity level. The NMES device (201) can be switched on and off by pressing the power button (202) which can also be used to select the stimulation program/treatment. The stimulation intensity can be set by pressing the PLUS and MINUS buttons (203). The intensity level is displayed on the LEDs located on the side of the device (204).

The NMES device is powered by a rechargeable battery which can be charged by a USB adapter or wirelessly.

Wearable Support

The NMES devices are attached to wearable supports. These supports can be in the form of garments such as shirt, pants, shorts, gloves or socks or in the form of accessories such as straps, wraps or sleeves. The conductive material is rendered on top of the inner layer of the garment or accessory. The garments are made of compression textile to ensure an optimal contact between the conductive material rendered into the garment and the skin of the individual to be stimulated. The conductive material can be made of carbon, graphene or other conductive material such as conductive ink.

The NMES devices can attached to the wearable supports by means of magnetic snaps or mechanical snaps. The snaps are configured for releasable mounting of the NMES device on the wearable support. If mechanical, flexibility of one or both of the connectors (i.e. one or both of the male and female connector parts of the snap) may be used to achieve releasable mounting. A hook-type mechanical arrangement could also be used. Mechanical and magnetic snap fittings may be used in combination with one another to achieve a more secure attachment. Mounting, as used herein, refers to connection of the NMES device to the wearable support which retains the NMES device in its connected location. Mounting may therefore be a sufficiently strong connection to retain the NMES device in place against the effect of gravity (for example if an NMES device is mounted to a shirt and the user is upright, the mounting must not allow the NMES device to pivot and fall off the support). Mounting may also refer to a sufficiently strong connection so as to retain the NMES device in place despite movement of the user, for example during a session of exercises or during stimulated contraction of the muscle lying underneath the mounting. The mounting is releasable in that it can be removed by the user, by applying force in a specific manner, or by implementing a rotation alongside a pulling force away from the wearable support, for example.

Carbon Electrodes

The electrode pads rendered into the inner layer of the garments have a specific design allowing the effective delivery of the electrical stimulation impulses to the targeted muscle groups and preserving the stretchability of the supporting fabric.

FIG. 4 represents the electrode pads design for the smart shirt. The different targeted muscle groups are the pectoral muscles (301), the abdominal muscles (302), the shoulder muscles (303), the triceps muscles (304), the biceps muscles (305), the upper back muscles (306), the middle back muscles (307) and the lower back muscles (308). The pectoral, abdominal and all back muscle groups are separated into left and right areas.

Figure 5:
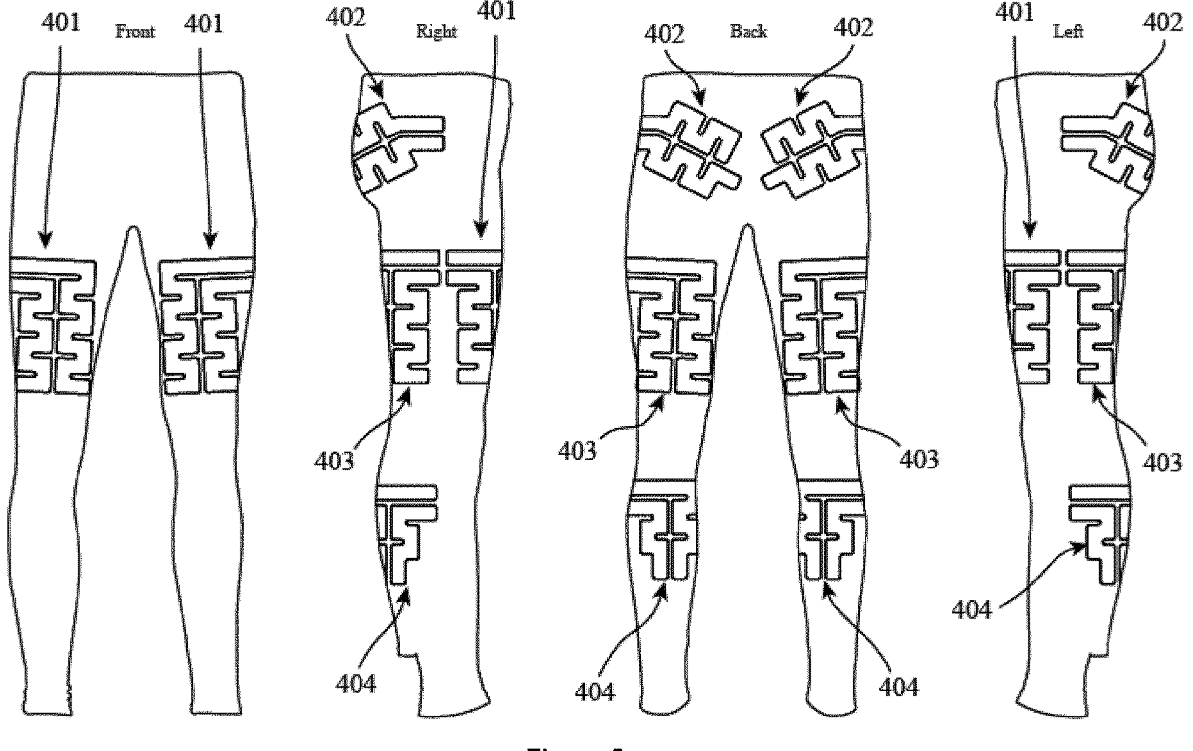
FIG. 5 shows four views of a wearable support, a pair of trousers/pants, in accordance with an embodiment of the invention.

FIG. 5 represents the design of the electrode pads for the pants. The different targeted muscle groups are the quadriceps (401), the gluteus (402), the hamstrings (403) and the calf muscles (404).

RFID Tag

Figure 6:
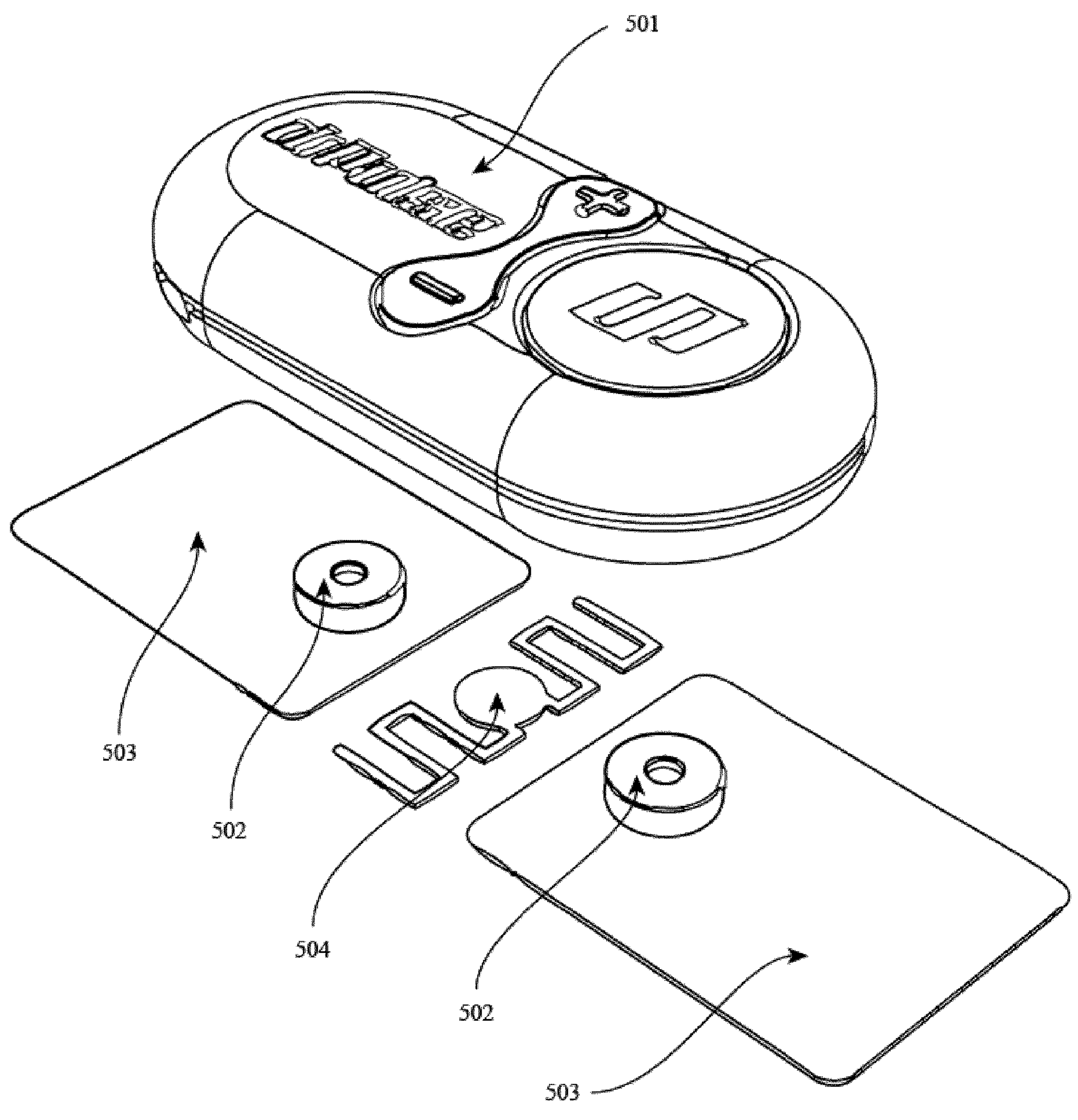
FIG. 6 shows a controller device, identifier, and conductive media in accordance with an embodiment of the invention.

Radio-frequency identification (RFID) tags can be placed on the wearable supports. This RFID tag will be located between the snaps that are used to attached the NMES device to the wearable support. FIG. 6 represents a RFID tag (504) placed between two electrode pads made of conductive material (503). The NMES device (501) will attach to the wearable support by the mean of magnetic or mechanical snaps (502). The NMES device will read the RFID using Near Field Communication (NFC) which will provide data about the type of wearable supports (shirt, pants, strap, sleeve . . . ) and the muscle group to be stimulated (right arm, left shoulder, lower right back . . . ).

As depicted, the snaps 502 (also referred to herein as device connectors) are attached directly to the conductive material 503 (also referred to herein as conductive media)—in this embodiment of the invention there are two electrode pads for a single identifier 504. It will be appreciated that alternative combinations of conductive material 503, snaps 502, and identifier 504 are anticipated. Furthermore, the snaps 502 need not be connected directly to the conductive material 503 as shown, and may be connected to the wearable support in another manner, for example secured to non-conductive fabric proximal the relevant conductive material 503.

Mobile Application

Figure 7:
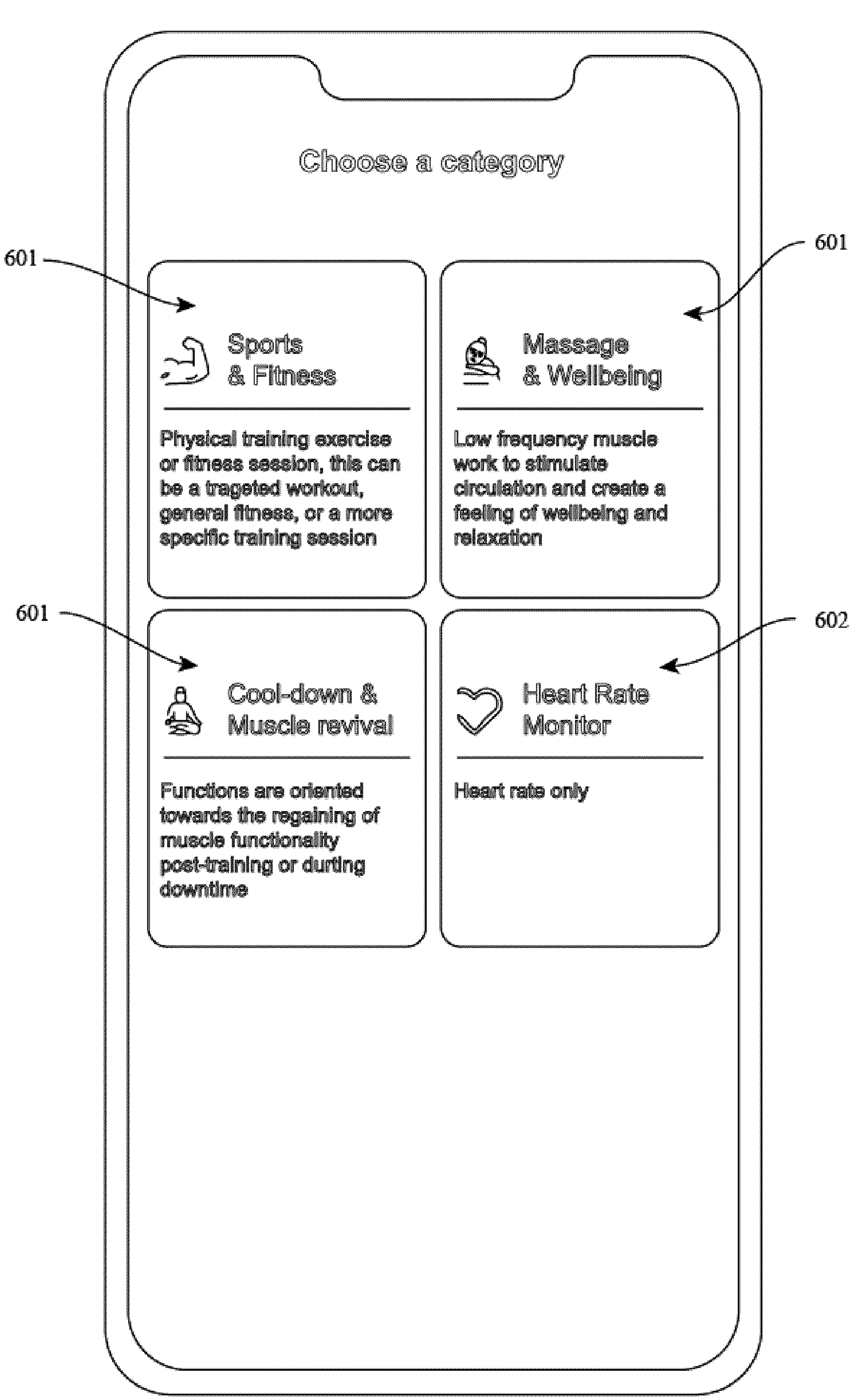
FIG. 7 shows a category selection screen within a mobile application in accordance with an embodiment of the invention.

The mobile application operates on iOS and Android mobile devices. It allows its operator to perform the following operations:

- At first launch of the mobile application
  - Accept the general conditions and privacy of the application.
  - Enter the date of birth, weight and gender of the user.
  - Download the default stimulation programs/treatments.
- After first launch
  - Run a stimulation program/treatment by performing the following steps:
    - Select a program/treatment category.
    - Select and stimulation program/treatment.
    - Select a garment or accessory on which the NMES devices will be attached.
    - Connect the NMES devices and define their locations.
    - Group NMES devices.
    - Start the stimulation program/treatment.
    - Set the intensity of the NMES devices altogether or individually.
    - Skip between the different stages of the stimulation program/treatment
    - Stop the stimulation program/treatment before the predefine duration if needed.
    - View a report of the session.
  - Connect additional sensors such as heart rate monitor or motion sensing and visualize their data.
  - Register his NMES devices.
  - Update the firmware of the NMES devices.
  - View usage statistics.
  - Access the online shop to buy physical accessories.
  - Access the online store to buy more stimulation programs/treatments
    - The stimulation program/treatment can be purchased permanently.
    - The stimulation program/treatment can be purchased for a limited number of sessions.
    - A single use sample of the stimulation program/treatment can be provided free of charge to allow the user to test the program before buying it.
  - Connect a smart watch to the mobile application
  - Connect to an Apple Health or Google Fit account Select and Run a Stimulation Program After launching the mobile application, the category selection screen is displayed. The user can select one of the available categories each containing a set of stimulation programs. FIG. 7 shows the category selection screen where each category is listed and briefly described (601). There could also be other non-stimulation-oriented options such as only monitoring the user heart rate (602).

Figure 8:
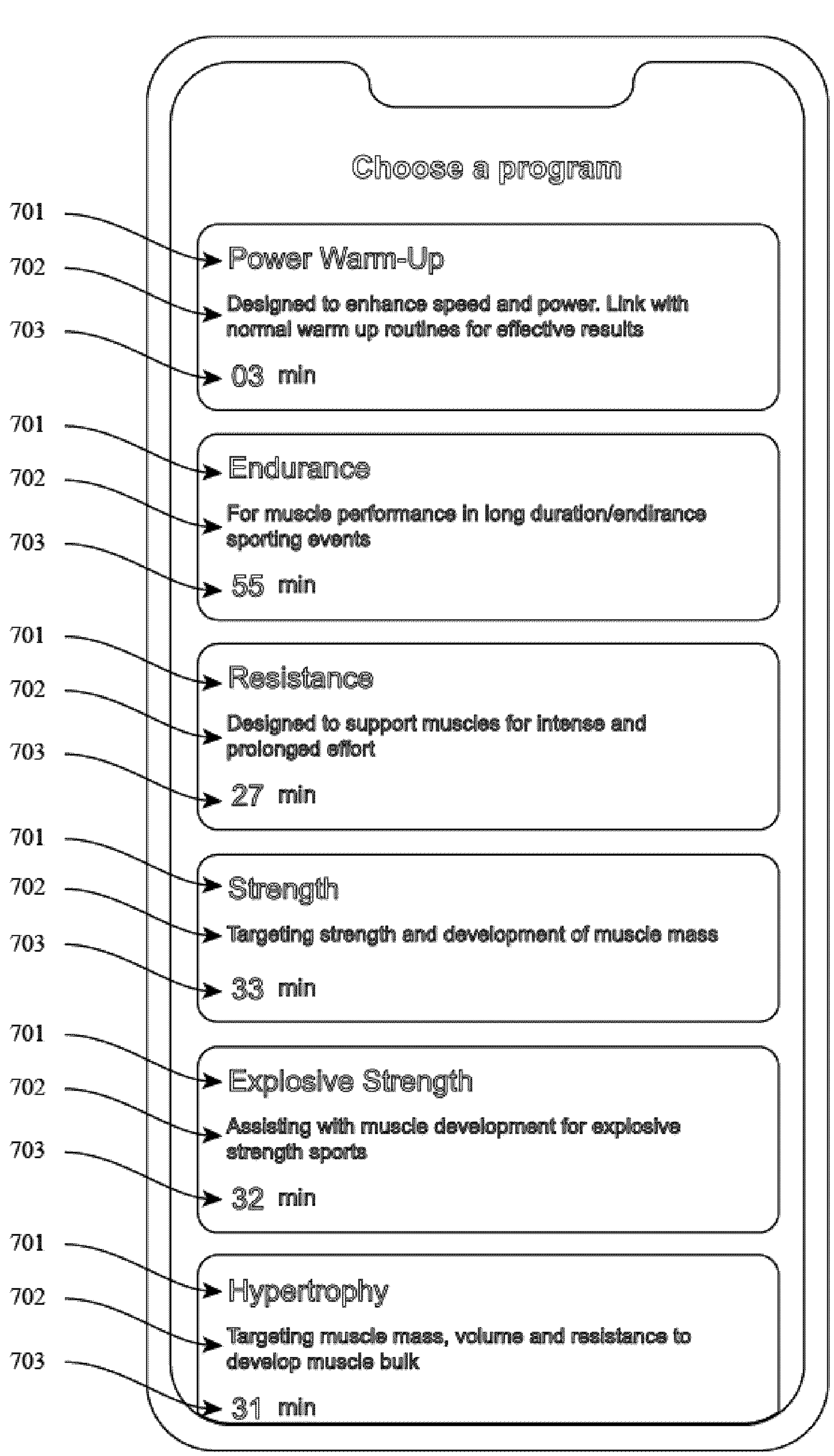
FIG. 8 shows a program/treatment selection screen within a mobile application in accordance with an embodiment of the invention.

After selecting the desired category, a list of available stimulation programs/treatments is displayed. The user can select a specific program by clicking on the corresponding field. FIG. 8 shows the program/treatment selection screen. The name (701), brief description (702) and duration (703) are provided for each program/treatment.

Figure 9:
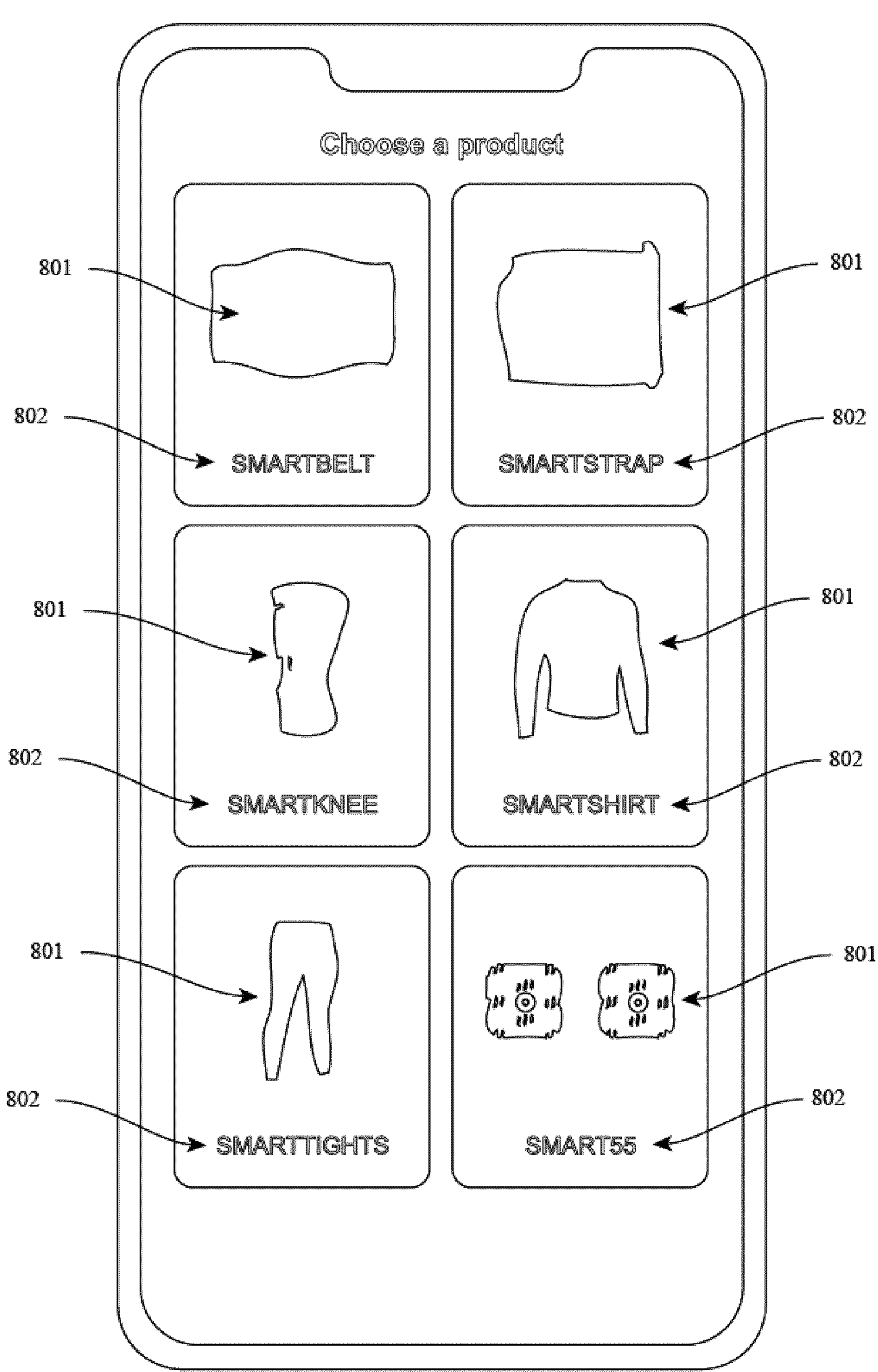
FIG. 9 shows a product selection screen within a mobile application in accordance with an embodiment of the invention.

After selecting the desired program/treatment, a list of available products consisting in garments or accessories which can be used with the selected program is displayed. This list can vary depending on the selected program. FIG. 9 shows the product selection screen where each allowed products is identified by a graphical view (801) and a name (802).

Figure 10:
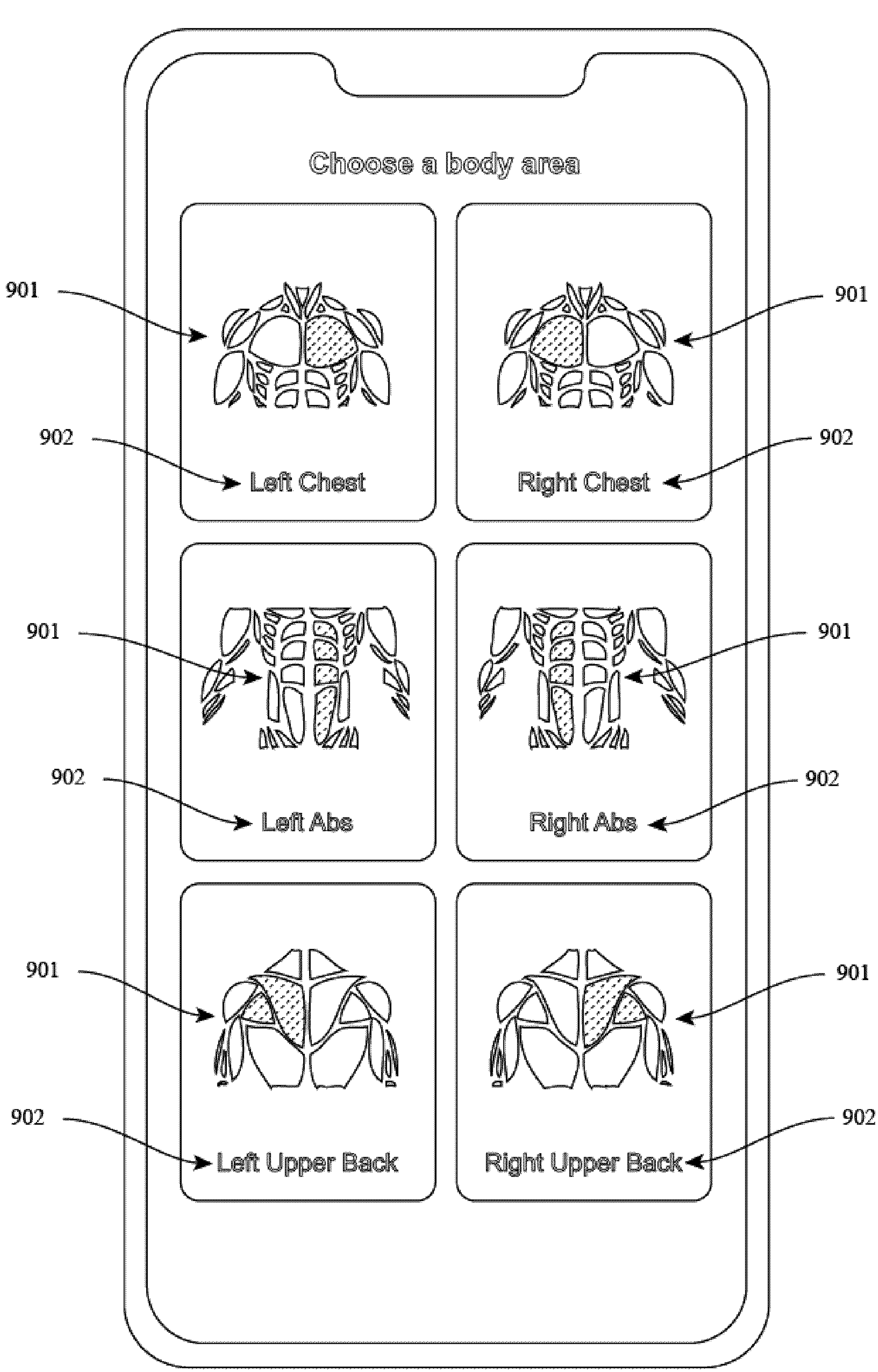
FIG. 10 shows an emplacement or body area selection screen within a mobile application in accordance with an embodiment of the invention.

After selecting the wearable support or product, the user is invited to connect the NMES devices. If the wearable support offers many emplacements to attach the NMES devices, the user will have to first select the location of the NMES device. FIG. 10 shows the emplacement or body area selection screen where each available emplacement is identified by a graphical representation (901) and a name (902).

Figure 11:
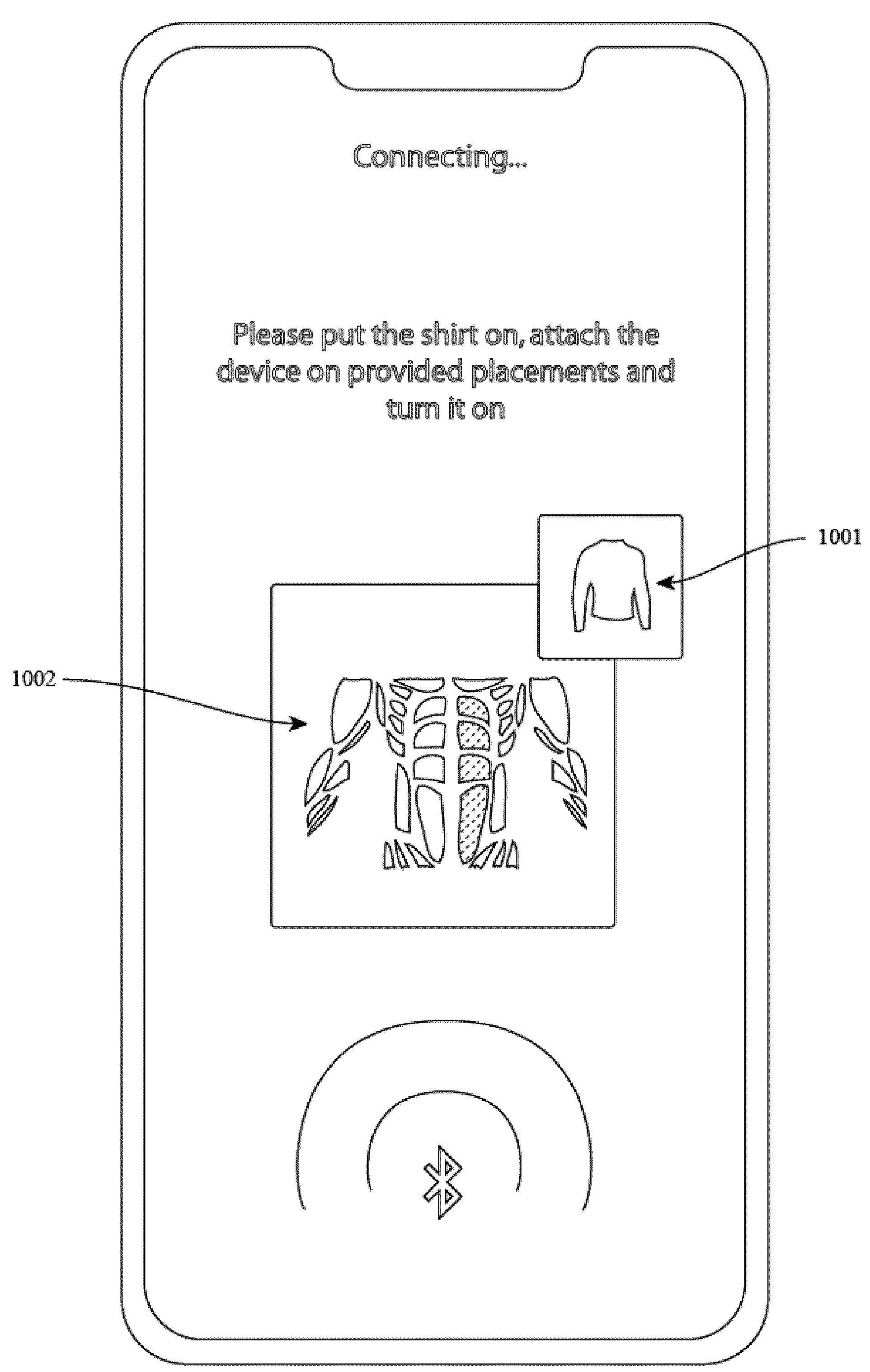
FIG. 11 shows a controller device connect screen within a mobile application in accordance with an embodiment of the invention.

After selecting the emplacement, the user is invited to connect the corresponding NMES device. FIG. 11 shows the NMES device connect screen where the selected product (1001) and emplacement (1002) are displayed.

Figure 12:
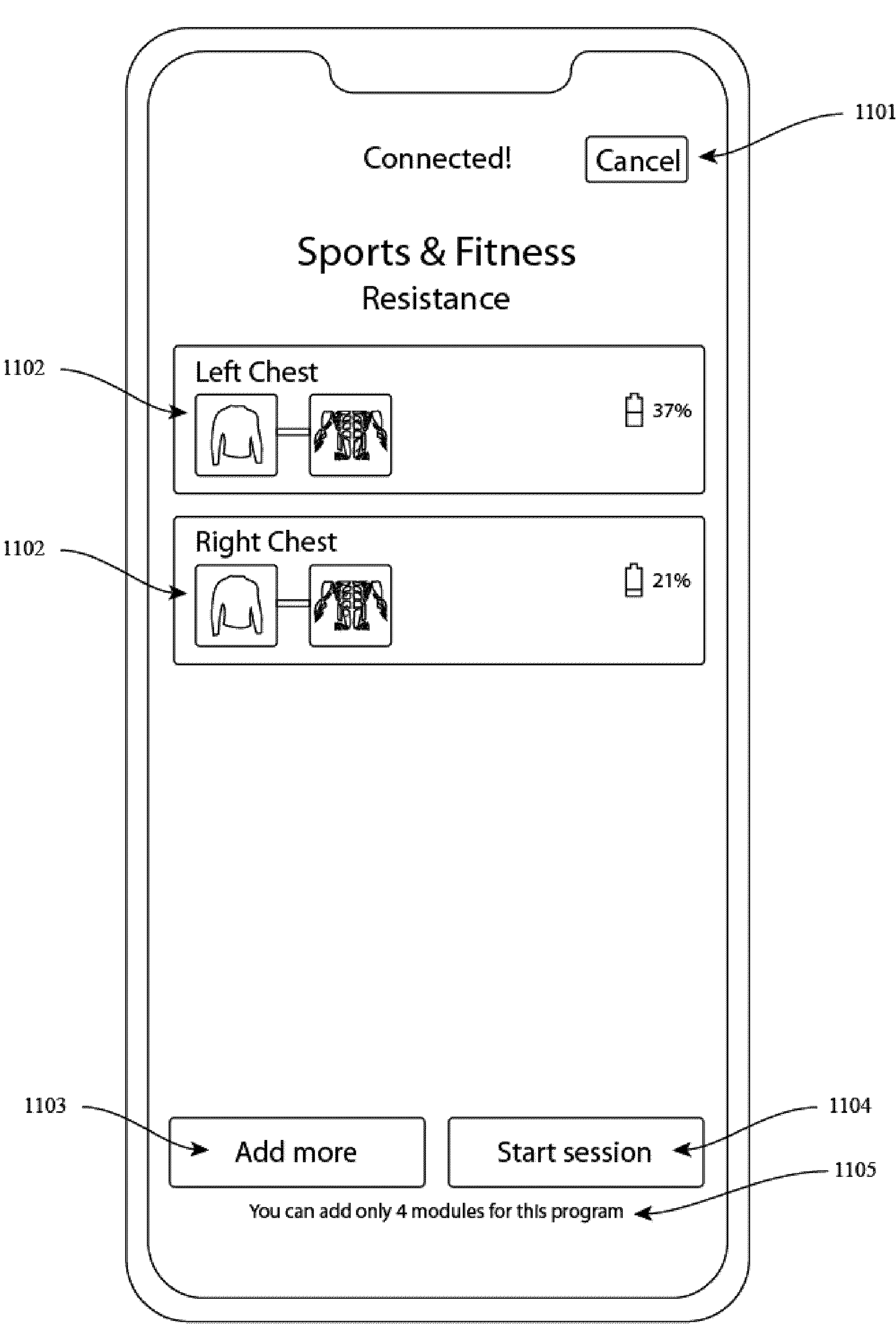
FIG. 12 shows a connected devices list screen within a mobile application in accordance with an embodiment of the invention.

After connecting a NMES device, the list of connected NMES devices is displayed to the user. FIG. 12 shows the connected devices list screen where the connected NMES devices are list (1102). The user can either cancel the session (1101), add more NMES devices (1103) or start the session (1104). The maximum number of NMES devices that can be connected is also displayed (1105).

Figure 13:
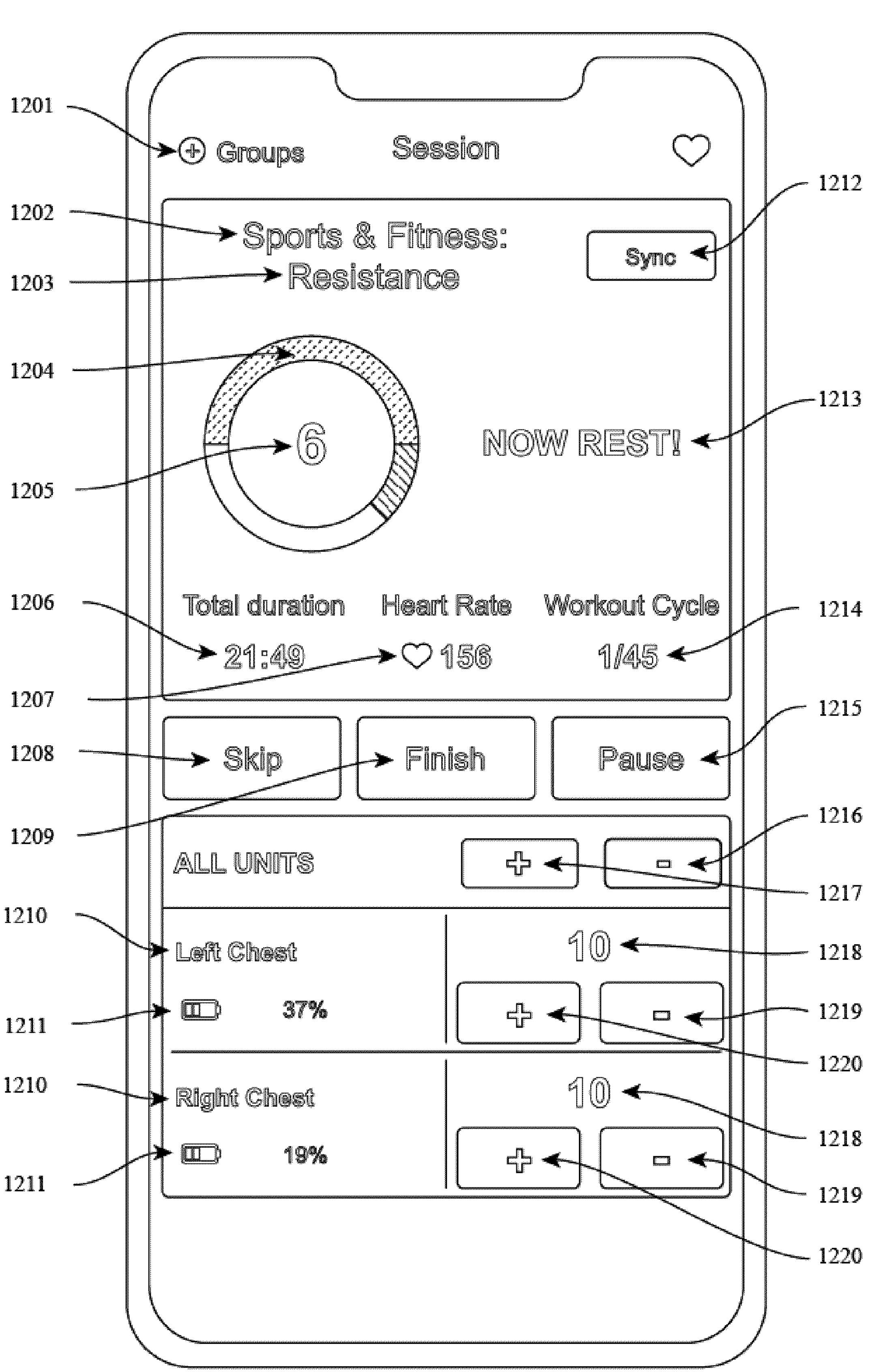
FIG. 13 shows a session screen within a mobile application in accordance with an embodiment of the invention.

Once the session is started, the session screen is displayed. FIG. 13 shows the session screen. The information made available to the user during the stimulation session are the program category (1202), program name (1203), if available the graphical representation of the contraction/rest cycle (1204), the remaining duration of the actual contraction or rest cycle (1205), the state of the actual contraction/rest cycle (1213), the total remaining duration (1206), if available the heart rate of the user (1207), if available the actual number of the contraction/rest cycle and the total number of cycles (1214). The emplacement/body area of each connected NMES device (1210), the battery level of each connected NMES device (1211) and the stimulation intensity of each connected NMES device (1218). During the stimulation session the user can perform different operations such as grouping NMES devices to control their intensity in one single operation (1201), synchronizing the NMES devices in case the user senses a delay between them (1212), if available skip to the next stage of the stimulation program (1208), finish the stimulation program (1209), pause/resume the stimulation program (1215), increase (1217) or decrease (1216) the intensity of all connected NMES devices, increase (1220) or decrease (1219) the intensity of a specific NMES device.

Figure 14:
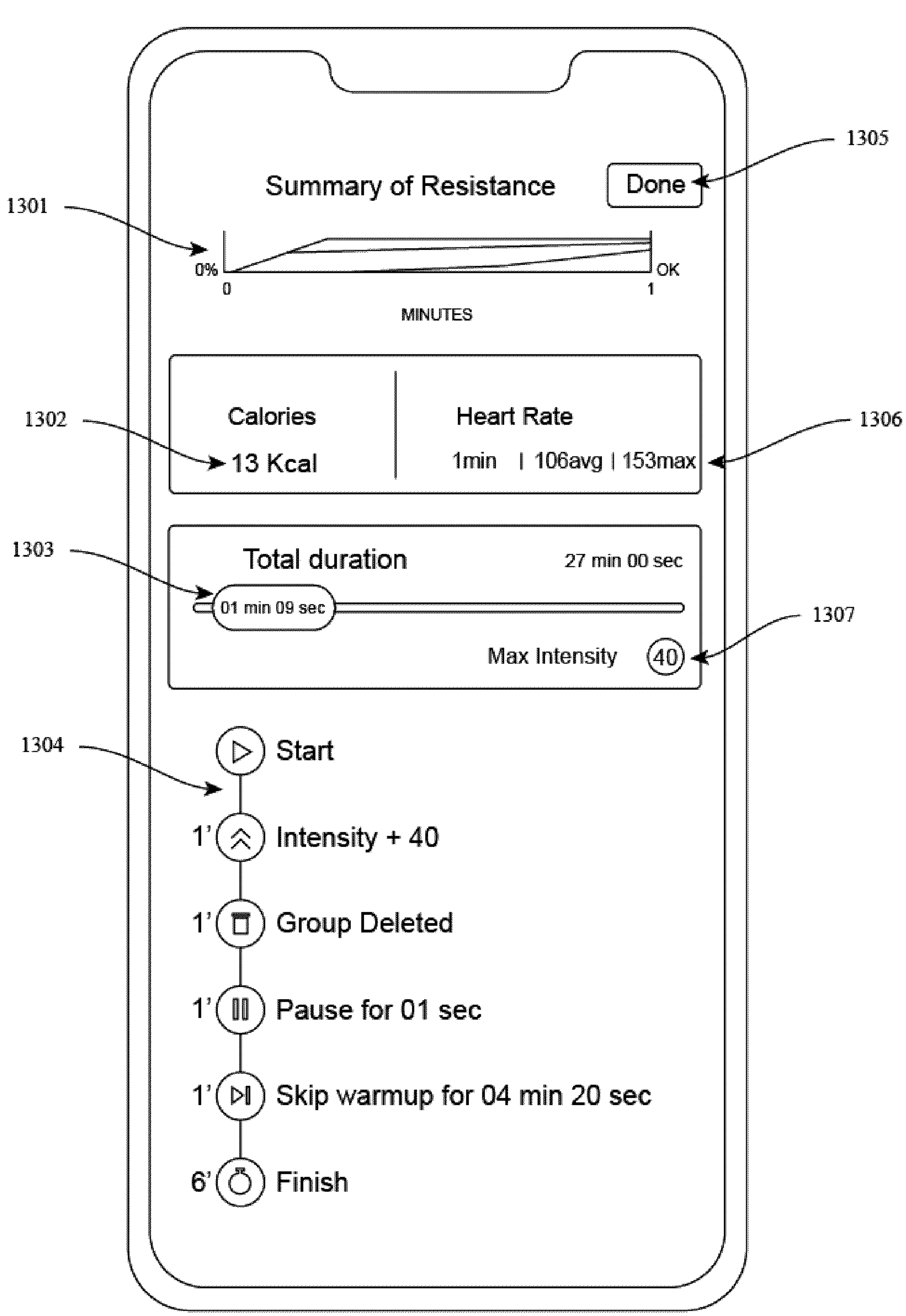
FIG. 14 shows a session screen within a mobile application in accordance with an embodiment of the invention.

At the end of the stimulation session, the session summary is displayed. FIG. 14 shows the session summary screen. The information displayed to the user are a graphical view of the intensity percentage during the session (1301), an estimate of the corresponding calories expenditure (1302), if available the maximum and average heart rate values (1306), a movable cursor (1303) showing the maximum intensity at a given time during the session (1307), a summary of the different operations performed by the user during the session (1304) such as but not limited to setting the NMES devices intensity, pausing the session, skipping to the next stage of the stimulation program, grouping/de-grouping the NMES devices. The user can quit the summary screen by clicking the Done button (1305).

Figure 15:
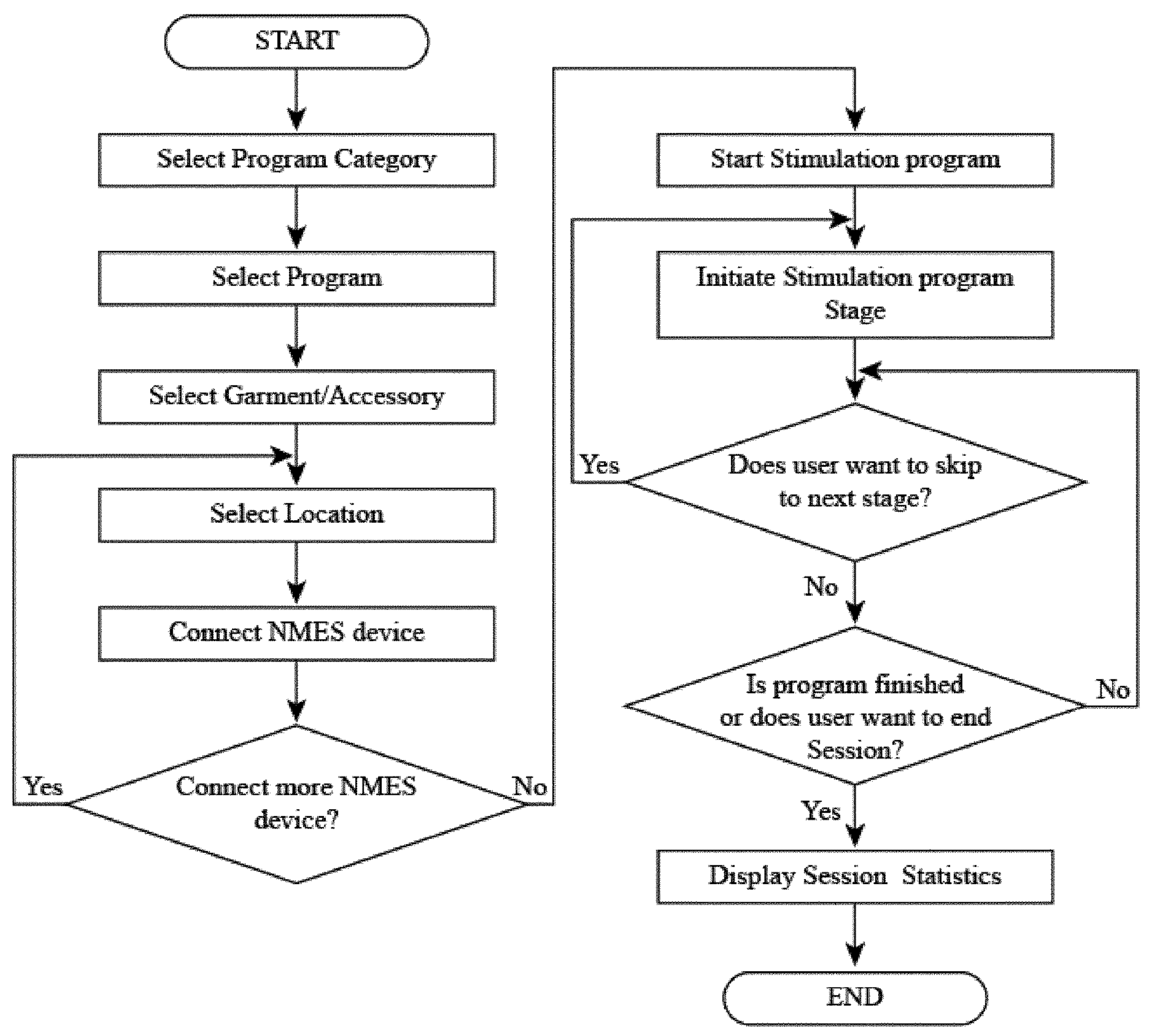
FIG. 15 shows a process flow of selecting and running a stimulation program/treatment in accordance with an embodiment of the invention.

FIG. 15 shows the process flow of selecting and running a stimulation program/treatment.

EMBODIMENTS

1. A system for stimulation of muscles and nerves, comprising:
   one or multiple neuromuscular stimulation devices with embedded electronic and firmware capable of safe and effective transmission of electrical stimulation signals; and
   one or multiple wearable supports with electrically conductive materials rendered on the inside that could be presented as, but not limited to, a garment, a strap or a sleeve that enables safe and effective transmission of electrical stimulation signals; and
   an application running on a mobile device such as a smartphone or a tablet allowing the selection of the stimulation treatments and the control and monitoring of the neuromuscular stimulation devices connected to the application through the Bluetooth Low Energy (BLE) interface.
2. A system for providing wireless electrical stimulation to muscles and nerves of a stimulated object (individual).
3. The system of embodiment 2 wherein the electrical stimulation is delivered by one or multiple wireless neuromuscular electrical stimulation devices.
4. The system of embodiment 2 wherein the neuromuscular electrical stimulation devices are attached to one or multiple wearable supports.
5. The system of embodiment 2 wherein the wearable support has electrically conductive materials rendered on the inside allowing the safe and efficient delivery of the electrical stimulation impulses to the stimulated object (individual).
6. The system of embodiment 2 wherein the electrically conductive material is rendered into the wearable support using a specific design preserving the stretchability and flexibility of the wearable support.
7. The system of embodiment 2 wherein the electrical stimulation impulses are delivered using constant voltage or constant current regulated technology.
8. The system of embodiment 2 wherein the neuromuscular electrical stimulation devices are controlled by a dedicated application running on a mobile device such as a smartphone or tablet.
9. The system of embodiment 2 wherein the neuromuscular electrical stimulation devices connect to the mobile device by means of Bluetooth Low Energy (BLE) area network technology.
10. The system of embodiment 2 wherein the electrical stimulation impulses delivered by the neuromuscular electrical stimulation devices are synchronized by the mobile application.
11. The system of embodiment 2 wherein the stimulation treatments are wirelessly transferred from the mobile application to the neuromuscular electrical stimulation devices.
12. The system of embodiment 2 wherein the mobile application allows for the selection of stimulation treatments.
13. The system of embodiment 2 wherein the mobile application allows for the purchase of stimulation treatments.
14. The system of embodiment 2 wherein the mobile application allows for the saving of performed stimulation treatments.
15. The system of embodiment 2 wherein the mobile application allows for the optional monitoring of biofeedback data provided by sensors attached to the user such as, but not limited to, heart rate, electromyography or body segment motion and orientation.
16. The system of embodiment 2 wherein the neuromuscular electrical stimulators attach to the wearable support and further connect to the electrically conductive material by means of magnetic or mechanical snap connectors.
17. The system of embodiment 2 wherein the Bluetooth interface protocol allows for simple cross integration into other existing systems for the treatment or improvement of muscular or medical condition.
18. The system of embodiment 2 wherein the Bluetooth interface protocol allows for simple cross integration into virtual reality applications for the treatment of muscular or medical condition as well as for virtual environment simulation for gaming, training, learning or entertainment purposes.

The invention claimed is:

1. A wearable support for facilitating provision of electrical stimulation to a user, the wearable support being configured to connect electrically to a controller device, the wearable support comprising:
   a device connector configured to receive a complimentary support connector of the controller device, wherein the device connector is configured to permit releasable mounting of the controller device on the wearable support;
   an identifier, configured to provide data to a processor on the controller device; and
   a conductive medium configured to contact the user and apply the electrical stimulation;
   wherein the conductive medium and the identifier are located in proximity to one another on the wearable support.

2. The wearable support of claim 1, wherein the wearable support comprises a garment or a wearable accessory, optionally wherein the garment or wearable accessory is: a shirt; pants; a glove; a sock; a strap; a wrap; or a sleeve.

3. The wearable support of claim 1, wherein the conductive medium is embedded within the garment or wearable accessory.

4. The wearable support of claim 1, wherein the conductive medium comprises an electrode pad, optionally wherein the electrode pad comprises: a carbon-based electrode; a graphene-based electrode; and/or conductive ink.

5. The wearable support of claim 1, wherein the device connector is configured such that, when the controller device is mounted on the wearable support, an electrical connection is established between the controller device and the wearable support via the support connector and the device connector.

6. The wearable support of claim 1, wherein the identifier is configured to provide data to the controller device by being configured to be read via a near field communication protocol, optionally wherein the identifier is a radio frequency identification tag.

7. The wearable support of claim 1, wherein the data provided by the identifier to the controller device comprises a location of the identifier on the wearable support and/or the type of wearable support.

8. The wearable support of claim 1, further comprising one or more further identifiers, each configured to provide data to a processor on a controller device, and one or more further conductive media, each configured to contact the user and apply electrical stimulation, wherein each further conductive medium is located in proximity to a respective one of the further identifiers on the wearable support.

9. A system, comprising:

the wearable support for facilitating provision of electrical stimulation to a user according to claim 1; and a controller device for controlling provision of electrical stimulation to a user, the controller device being configured to connect electrically to the wearable support, the device comprising:

a support connector configured to receive the device connector of the wearable support, wherein the support connector is configured to permit releasable mounting of the controller device on the wearable support; and a processor configured to receive data from the identifier on the wearable support.

10. The system according to claim 9, further comprising:

a mobile device, in communication with the controller device, the mobile device being configured to receive data from the controller device and to transmit data to the controller device.

11. The system according to claim 10, wherein the mobile device and controller device are configured to communicate via Bluetooth Low Energy.

12. The system of claim 9, wherein the controller device further comprises one or more user controls for controlling provision of electrical stimulation to the user, optionally wherein the one or more user controls comprise one or more of: an on button; an off button; an on/off button; an intensity increase button; and an intensity decrease button.

13. The system of claim 9, wherein the controller device further comprises a power source, optionally wherein the power source comprises a rechargeable battery.

14. The system of claim 9, wherein the controller device further comprises a visual indicator, optionally wherein the visual indicator comprises a strip of light emitting diodes.

15. The system of claim 9, wherein the processor is further configured to initiate an electrical stimulation program.

16. The system of claim 9, wherein the controller device further comprises a pulse generator configured to provide electrical current to the user via the wearable support.

17. The system of claim 9, wherein the support connector is configured such that, when the controller device is mounted on the wearable support, an electrical connection is established between the controller device and the wearable support via the support connector and the device connector.

18. The system of claim 9, wherein the processor is configured to receive data from the wearable support by reading an identifier on the wearable support via a near field communication protocol, optionally wherein the near field communication protocol is radio frequency identification.

* * * * *